United States Patent
Effing

(10) Patent No.: US 8,118,793 B2
(45) Date of Patent: *Feb. 21, 2012

(54) MEDICINAL COMPOSITION WITH ACTIVE INGREDIENTS AND WOUND CONTACT LAYER WITH A COMPOSITION

(75) Inventor: Jochem Effing, Kelkheim-Fischbach (DE)

(73) Assignee: Paul Hartmann AG, Heidenheim (DE)

( * ) Notice: Subject to any disclaimer, the term of this patent is extended or adjusted under 35 U.S.C. 154(b) by 600 days.

This patent is subject to a terminal disclaimer.

(21) Appl. No.: 12/140,583

(22) Filed: Jun. 17, 2008

(65) Prior Publication Data

US 2008/0249486 A1    Oct. 9, 2008

Related U.S. Application Data

(63) Continuation of application No. PCT/EP2006/012102, filed on Dec. 15, 2006.

(30) Foreign Application Priority Data

Dec. 17, 2005   (DE) .................. 10 2005 060 461

(51) Int. Cl.
  *A61F 13/00* (2006.01)
(52) U.S. Cl. ........................................ 604/304; 514/779
(58) Field of Classification Search ............ 604/19, 604/27, 46, 48, 289, 304–308, 332, 336; 514/969, 7.6, 16.5, 20.9, 154, 565, 600, 626; 424/141.1, 94.1, 409, 618, 777–781; 602/41, 602/48, 58; 428/40.1, 40.2, 40.5, 40.6
See application file for complete search history.

(56) References Cited

U.S. PATENT DOCUMENTS

| | | | |
|---|---|---|---|
| 3,972,328 A * | 8/1976 | Chen | 602/56 |
| 4,503,034 A * | 3/1985 | Maupetit et al. | 424/78.05 |
| 5,681,579 A | 10/1997 | Freeman | |
| 6,375,977 B1 * | 4/2002 | Auguste et al. | 424/447 |
| 6,794,555 B2 * | 9/2004 | Apert et al. | 602/48 |
| 2004/0049145 A1 | 3/2004 | Flick | |
| 2005/0084647 A1 * | 4/2005 | Menzies et al. | 428/99 |
| 2005/0142154 A1 * | 6/2005 | Blatt et al. | 424/401 |
| 2005/0281762 A1 | 12/2005 | Modak et al. | |
| 2008/0249453 A1 * | 10/2008 | Effing | 602/48 |
| 2008/0249485 A1 * | 10/2008 | Effing | 604/304 |
| 2008/0249486 A1 * | 10/2008 | Effing | 604/304 |

FOREIGN PATENT DOCUMENTS

| | | |
|---|---|---|
| DE | 10 2004 03195 | 1/2006 |
| DE | 102004031955 A1 | 1/2006 |
| EP | 65399 A1 | 5/1982 |
| EP | 0 065 399 | 11/1982 |

(Continued)

OTHER PUBLICATIONS

International Search Report of PCT/EP2006/012102 Mailed on May 9, 2007 (4 pages).

*Primary Examiner* — Tatyana Zalukaeva
*Assistant Examiner* — Benedict L. Hanrahan
(74) *Attorney, Agent, or Firm* — Brinks Hofer Gilson & Lione

(57) ABSTRACT

The invention relates to a wound dressing, a wound contact layer and a medicinal composition comprising a hydrophilic base in which hydrocolloids are dispersed, wherein the hydrophilic base comprises at least one emulsifier and the use of said composition for treating wounds.

15 Claims, 1 Drawing Sheet

FOREIGN PATENT DOCUMENTS

Figure 1:
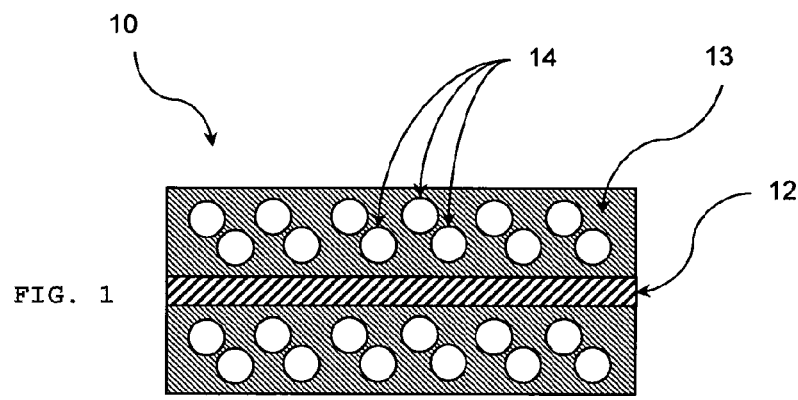

| | | |
|---|---|---|
| EP | 0 107 526 | 5/1984 |
| EP | 0107526 A1 | 5/1984 |
| EP | 0 621 031 | 10/1994 |
| EP | 621031 A2 | 10/1994 |
| EP | 1159972 A2 | 5/2001 |
| EP | 1 159 972 | 12/2001 |
| EP | 1 535 605 | 6/2005 |
| EP | 1535605 A1 | 6/2005 |
| WO | 96/036315 A | 5/1996 |
| WO | WO 96/36315 | 11/1996 |
| WO | WO 01/60599 | 8/2001 |
| WO | 0170285 A1 | 9/2001 |
| WO | WO 01/70285 | 9/2001 |
| WO | 03066001 A2 | 8/2003 |
| WO | WO 03/066001 | 8/2003 |
| WO | 2005009403 | 2/2005 |
| WO | WO 2005/009403 | 2/2005 |

* cited by examiner

MEDICINAL COMPOSITION WITH ACTIVE INGREDIENTS AND WOUND CONTACT LAYER WITH A COMPOSITION

CROSS-REFERENCE TO RELATED APPLICATIONS

This application is a continuation of International Application No. PCT/EP2006/012102 filed on Dec. 15, 2006, which claims the benefit of DE 10 2005 060 461.7, filed Dec. 17, 2005. The disclosures of the above applications are incorporated herein by reference.

FIELD

The present invention relates to a medicinal composition and use thereof for treating wounds.

BACKGROUND

The statements in this section merely provide background information related to the present disclosure and may not constitute prior art.

A wide variety of ointments and other compositions for use in human treatment have been known and used over the past decades. These ointments are usually semi-solid compositions that are intended for use on healthy skin or some mucosae, on the eyes, for example. These ointments or preparations should mostly have a local effect, deliver active ingredients percutaneously, or have a softening or protective effect on the skin.

Furthermore, numerous ointments for the treatment of wounds are known. EP 621 031 describes an ointment which is formulated as a gel and at least comprises a gel-forming polysaccharide and hexylene glycol. Carboxymethylcellulose or sodium alginate is to be used as a gel-forming polysaccharide. This composition apparently has an antimicrobial effect and is not toxic upon contact with fibroplasts.

Moreover, EP 107 526 describes a skin protective paste for the treatment of wounds or stoma care, for example, which, formulated as a gel, comprises polyvinyl pyrrolidone, carboxymethylcellulose, alginate, water, an oil, and a fatty acid ester. This gel contains at least 20 weight percent of water and at least 45 weight percent of hydrocolloids.

Furthermore, hydrophilic ointments are known that absorb a limited amount of water and may be used for the treatment of wounds. These ointments contain a mixture of different mono-, di- and triglycerides and a nonpolar oil and are included in Atrauman® on carrier materials for the production of so called ointment dressings, for example.

From EP 65 399, a sterile wound dressing is further known that comprises a carrier material impregnated with an antiseptic ointment and a water soluble polyvinyl pyrrolidone film. The ointment may be a hydrophilic or hydrophobic ointment.

From WO 96/036 315, a sterilizable paste or cream is known, which comprises an emulsion and a water insoluble, gel-forming material that may be cross-linked carboxymethylcellulose. The emulsion for its part is said to comprise an oil or wax, water, and an emulsifier, the water content being at least 40 weight percent.

A compress for wound treatment is known from WO 01/070 285, which comprises a hydrophobic elastomer matrix, into which the hydrocolloid particles are dispersed. Further, the matrix is said to have 55 to 90 weight percent of a nonpolar oil and a surface-active agent with an HLB value greater than 10.

SUMMARY

The present disclosure includes a medicinal composition, which comprises 50 to 99 weight percent of a hydrophilic base, into which about 1 to about 50 weight percent of hydrocolloids are dispersed, which at least comprise one releasable, wound healing substance, about 0.5 to about 50 weight percent of the hydrophilic base comprising at least one emulsifier. These objects are further attained by means of a wound contact layer, which comprises such a composition and a carrier material for the composition.

Here and below, in connection with the present disclosure, all content data are to be understood as weight percent based on the total mass of the medicinal composition, unless otherwise specified. Furthermore, in connection with the present invention, hydrophilic base is to be understood as a medicinal composition, which is a single- or multi-phase composition, and as a result of the content of at least one emulsifier is present as an emulsion, or is capable of forming an emulsion. Such emulsions may be emulsions that comprise at least one water and/or gel phase and at least one oil phase.

An advantage of this composition is that owing to the content of hydrocolloids that are dispersed in the hydrophilic base, the composition is capable of absorbing an especially large volume of fluids, like wound exudates, very rapidly. The hydrophilic base forms an emulsion on contact with fluids within a short time, whereupon in a second step the water in the emulsion is absorbed by the dispersed hydrocolloids of the base. This process may also take place in parallel. In any case, besides the emulsion that is being formed, the hydrocolloids form a second fluid reservoir. In this connection, the release of the wound healing substance is controlled, inter alia, by the absorption of wound exudate. The more wound exudate is absorbed by the hydrophilic base or the hydrocolloids, the more wound healing substance is released. Hence, the hydrocolloids are a fluid reservoir and repository of the wound healing substance, which releases the wound healing substance in a controlled manner.

In another form of the medicinal composition, the composition comprises less than about 10 weight percent of water, in particular less than about 5 weight percent of water and is quite particularly preferably water-free. In particular, the hydrophilic base comprises less than about 10 weight percent of water, in particularly less than about 5 weight percent, and is quite particularly water-free in one form of the present disclosure. This hydrophilic base is thus present as a single-phase mixture and as a result of the presence of at least one emulsifier, is capable of forming an emulsion upon addition of water, for example. In connection with the present disclosure, it is hereby and hereinafter meant that the hydrophilic base may contain traces of water, where the water content should be at most about 1 weight percent based on the mass of the hydrophilic base.

In another form, the composition comprises a hydrophilic base, which is a cream, a cream base or an ointment. In particular, the hydrophilic base is a hydrophilic cream or cream base or a hydrophilic ointment. Within the context of this application, an ointment is to be understood as a single-phase system, whereas a cream is a two-phase or multiphase system. An exact differentiation of these formulations, as well as the definition of further formulations, are provided in the German Pharmacopeia DAB 9 and comments, which are expressly referenced here.

Further, it is particularly provided that the composition comprises a hydrophilic base, further comprising about 1 to about 40 weight percent of nonpolar lipids. The composition in particular comprises a hydrophilic base, which further comprises about 10 to about 40 weight percent, further in particular about 10 to about 30 weight percent of nonpolar lipids, and further quite particularly preferably about 10 to about 25 weight percent of nonpolar lipids.

Within the scope of the present disclosure, "lipids" is used as the generic term for fats, oils, waxes, and the like. The terms "oil phase" and "lipid phase" are also used as synonyms. Lipids differ, inter alia, in their polarity. It has already been proposed to adopt the interfacial tension with respect to water as a measure of the polarity of a lipid and/or lipid phase. This means that the polarity of the lipid phase in question is greater, the lower the interfacial tension between this lipid phase and water. According to the present invention, the surface tension is regarded as one possible measure of the polarity of a given oil component. The interfacial tension is that force which acts on an imaginary line one meter in length in the interface between two phases. The physical unit for this interfacial tension is conventionally calculated according to the force-length relationship, and is usually stated in mN/m (millinewtons divided by meters). It has a positive sign if it tends to reduce the interface. In the reverse case, it has a negative sign. According to the present disclosure, 20 mN/m is the interfacial tension with respect to water below which lipids are regarded as polar, and 30 mN/m is the interfacial tension with respect to water above which lipids are regarded as nonpolar. Lipids having a surface tension with respect to water between 20 and 30 mN/m are generally regarded as midpolar.

Nonpolar lipids are those lipids which are chosen from the group of branched or unbranched hydrocarbons and hydrocarbon waxes, in particular Vaseline, petrolatum, paraffin oil, mineral oil, polyisobutene, wax, or combinations thereof.

Besides nonpolar lipid components, the hydrophilic base according to the invention may also contain polar and midpolar lipids. Polar or midpolar lipids are for example those from the group of fatty acid triglycerides, fatty acid diglycerides, fatty acid monoglycerides, or fatty acid esters of glycerol oligomers, such as full or partial fatty esters of diglycerol or triglycerol. In particular, the tri-, di- and monoglycerides may be esters of saturated and/or unsaturated, branched and/or unbranched alkanecarboxylates with a chain length from 8 to 24, in particular 12 to 18 C-atoms. Fatty acid triglycerides, fatty acid diglycerides, fatty acid monoglycerides may, for example, be advantageously chosen from the group of synthetic, semi-synthetic and natural fats or oils.

In connection with the present disclosure, a mixture comprising one part polar or nonpolar lipids and at least one emulsifier at a concentration of about 0.5 to about 40 weight percent, in particular about 0.5-30 weight percent, may also be particularly considered as a hydrophilic base, whereby the proportion of midpolar and nonpolar lipids in the hydrophilic base relative to the nonpolar lipids is greater than about 1:1, in particular greater than about 2:1 and quite particularly between about 3:1 and about 10:1 based on the total lipid content.

In particular, a composition according to the present disclosure has a hydrophilic base comprising 20-80 weight percent of mono-, di-, and/or triglycerides and/or full or partial esters of glycerol oligomers based on the total weight of the composition. The hydrophilic base in particular comprises about 30-70 weight percent, and quite particularly about 40-70 weight percent of mono-, di- and/or triglycerides and/or full or partial esters of glycerol oligomers based on the total weight of the composition. In this case, it is especially advantageous if the composition comprises about 10-50 weight percent of mono-, di- and/or triglycerides and about 10-30 weight percent of partial esters of glycerol oligomers, in particular of diglycerol or triglycerol.

In a further especially preferred embodiment, a composition according to the invention comprises a hydrophilic basis comprising about 40-80 weight percent of monoglycerides, diglycerides, triglycerides and/or partial esters of glycerol oligomers, in particular of diglycerol or triglycerol, about 15-30 weight percent of nonpolar fats, and about 0.5-30 weight percent of emulsifier based on the total weight of the composition.

In yet another form of the present disclosure, a composition comprises a hydrophilic basis comprising about 40-80 weight percent of monoglycerides, diglycerides, triglycerides and/or partial esters of glycerol oligomers, in particular of diglycerol or triglycerol, about 15-30 weight percent of nonpolar fats, about 0.5-30 weight percent of emulsifier, and about 1-50 weight percent of hydrocolloids, which are dispersed into the hydrophilic base and at least comprise a releasable, wound healing substance.

In connection with the present disclosure, emulsifiers are understood to be substances which feature interfacial activity, such that, on addition of water to the hydrophilic base, a multiphase mixture, namely an emulsion, may be formed. A composition according to the present invention should in particular comprise at least one emulsifier, by means of which, on addition of water the hydrophilic base is capable of forming a water-in-oil emulsion (W/O emulsion), gel-in-oil emulsion (G/O emulsion), oil-in-water emulsion (O/W emulsion), oil-in-gel emulsion (O/G emulsion), water-in-oil-in-water emulsion (W/O/W emulsion), gel-in-oil-in-gel emulsion (G/O/G emulsion), gel-in-oil-in-water emulsion (G/O/W emulsion), water-in-oil-in-gel emulsion (W/O/G emulsion), oil-in-water-in-oil emulsion (O/W/O emulsion), or oil-in-gel-in-oil emulsion (O/G/O emulsion). Further preferred are emulsifiers that are capable of forming an O/W emulsion or W/O emulsion or O/G or G/O emulsion and are free from ethylene or propylene glycols or ethylene propylene glycols, i.e. do not comprise any substances that comprise any ethylene or propylene glycol or ethylene propylene glycol units.

In this case, the composition according to the present disclosure may particularly comprise at least about 0.5-50 weight percent of emulsifier, particularly at least about 0.5-40 weight percent of emulsifier, particularly at least about 0.5-30 weight percent of emulsifier, particularly at least about 1-20 weight percent of emulsifier, and quite particularly at least about 1-10 weight percent of emulsifier.

Thus in another form, the composition according to the disclosure comprises about 50 to about 99 weight percent of hydrophilic base, into which about 1 to about 50 weight percent of hydrocolloids are dispersed, which have at least one releasable, wound healing substance, about 0.5 to about 40 weight percent of the hydrophilic basis comprising at least one O/W emulsifier, in particular an ionic O/W emulsifier. However, it may also be provided that instead of the O/W emulsifier, a nonionic W/O emulsifier is used. In particular, this composition has less that about 10 weight percent of water and further comprises preferably a hydrophilic base, which comprises about 0.5 to about 30 weight percent of at least one O/W emulsifier, particularly an ionic O/W emulsifier, or a W/O emulsifier, particularly a nonionic W/O emulsifier.

In another form, a composition according to the disclosure comprises less than about 10 weight percent of water, about 60 to about 95 weight percent of hydrophilic base, into which up to about 40 weight percent of hydrocolloids are dispersed, about 0.5 to 50 weight percent of the hydrophilic base comprising at least one O/W emulsifier. However, it may also be provided that instead of the O/W emulsifier, a nonionic W/O emulsifier is used.

Using an emulsifier of the O/W type is advantageous in that when the composition is applied, the composition may very easily be completely washed off the wound by means of water, for example.

In yet another form, a composition according to the disclosure comprises less than about 10 weight percent of water, about 60 to about 95 weight percent of hydrophilic base, into which about 5 to about 40 weight percent of hydrocolloids are dispersed, which comprise at least one releasable, wound healing substance, about 0.5 to about 30 weight percent of the hydrophilic base comprising at least one O/W emulsifier or a nonionic W/O emulsifier.

A composition according to the present disclosure may further preferably contain a nonionic emulsifier with an HLB value from 3 to 18, according to the definitions given in Rompp Lexikon Chemie (Ed. J. Falbe, M. Regitz), 10th edition, Georg Thieme Verlag Stuttgart, New York, (1997), page 1764. According to the present invention, nonionic O/W emulsifiers with an HLB value from 10 to 15 as well as nonionic W/O emulsifiers with an HLB value from 3 to 6 are particularly preferred.

In particular, the emulsifier or emulsifiers, in particular nonionic O/W emulsifiers, may advantageously be chosen from the group:

Fatty alcohol ethoxylates having the general formula R—O—$(CH_2—CH_2—O)_n$—H or fatty alcohol propoxylates having the general formula R—O—$(CH_2—CH(CH_3)—O)_n$—H, where R is a branched or unbranched alkyl or alkenyl radical and n represents a number from 10 to 50, Ethoxylated or propoxylated lanolin alcohols, Polyethylene glycol ethers having the general formula R—O—$(CH_2—CH_2—O)_n$—R' or polypropylene glycol ethers having the general formula R—O—$(CH_2—CH(CH_3)—O)_n$—R', where R and R' are independently other branched or unbranched alkyl or alkenyl radicals and n is a number from 10 to 80, Fatty acid ethoxylates having the general formula R—O—$(CH_2—CH_2—O)_n$—H or fatty acid propoxylates having the general formula R—COO—$(CH_2—CH(CH_3)—O)_n$—H, where R is a branched or unbranched alkyl or alkenyl radical and n represents a number from 10 to 40, Etherified fatty acid ethoxylates having the general formula R—COO—$(CH_2—CH_2—O)_n$—R' or etherified fatty acid propoxylates having the general formula R—COO—$(CH_2—CH(CH_3)—O)_n$—R', where R and R' are independently branched or unbranched alkyl and alkenyl radicals and n is a number from 10 to 80, Esterified fatty acid ethoxylates having the general formula R—COO—$(CH_2—CH_2—O)_n$—C(O)—R' or esterified fatty acid propoxylates having the general formula R—COO—$(CH_2—CH(CH_3)—O)_n$—C(O)—R', where R and R' are independently branched or unbranched alkyl or alkenyl radicals and n represents a number from 10 to 80, Polyethylene glycol glycerol fatty acid ester or polypropylene glycol glycerol fatty acid ester of saturated and/or unsaturated, branched and/or unbranched fatty acids and an ethoxylation degree or propoxylation degree between 3 and 50, Ethoxylated or propoxylated sorbitan esters having an ethoxylation degree or propoxylation degree from 3 to 100, Ethoxylated or propoxylated triglycerides having an ethoxylation degree or propoxylation degree from 3 to 150, Fatty acid esters of polyoxyethylene sorbitol on the basis of branched or unbranched alkanic or alkenic acids and an ethoxylation degree from 5 to 100, of the sorbeth type, for example.

Further, within the scope of the present disclosure, nonionic W/O emulsifiers of the group of dicarbonic acid esters or tricarbonic acid esters are advantageous. Of these, esters of malonic acid, succinic acid, adipic acid are particularly suitable. Dicarbonic acid esters are further preferred, in particular succinic acid esters are suitable, which are formed with saturated or unsaturated and/or linear or branched C8-C24 fatty alcohols and/or glycerol as well as their oligomers, in particular diglycerol or triglycerol. Succinic acid esters with saturated and branched C8-C24 fatty alcohols and/or glycerol as well as their oligomers, in particular diglycerol or triglycerol, have proven particularly advantageous as nonionic W/O emulsifiers. Quite particularly suitable among them are dicarbonic acid esters, which are formed with succinic acid and saturated and branched C8-C24 fatty alcohols and diglycerol. According to the INCI nomenclature, one such emulsifier is designated isostearyl diglyceryl succinate and is available under the product name "Imwitor®780." These emulsifiers are further advantageous in that they are free from polyethylene glycol, i.e. do not comprise any ethylene glycol units.

In particular, ionic O/W emulsifiers may also be used as O/W emulsifiers in connection with the present invention. In particular as O/W emulsifiers, ionic O/W emulsifiers may advantageously be chosen from the group of monoglyceride and/or diglyceride esters of saturated or unsaturated fatty acids with hydroxycarbonic acids and/or tricarbonic acids. Partially neutralized monoglycerol and/or diglycerol esters of saturated fatty acids with hydroxycarbonic acids and/or tricarbonic acids, in particular of lactic acid and/or citric acid are especially preferred as O/W emulsifiers. Quite particularly preferred are lactic acid and/or citric acid esters, which, according to the INCI nomenclature are designated as glyceryl cocoate citrate lactate. Such emulsifiers are available under the product names "IMWITOR® 380" or "IMWITOR® 377", for example. These emulsifiers are further advantageous in that they are free from polyethylene glycol, i.e. do not comprise any ethylene glycol units.

According to the present disclosure, a hydrocolloid is to be understood as a material that is a hydrophilic synthetic or natural polymer material which is soluble or absorbent and/or swelling in water and form a gel. A composition according to the invention advantageously comprises a hydrocolloid of a synthetic or natural polymer material which is chosen from the group of alginic acid and its salts as well as its derivatives, chitin or its derivatives, chitosan or its derivatives, pectin, cellulose or its derivatives, such as cellulose ether or cellulose ester, linked or cross-linked carboxyalkylcellulose or hydroxyalkylcellulose, polyvinyl alcohol, polyvinyl pyrrolidone, agar, guar gum, or gelatin. Cellulose or its derivative or its salts, alginic acid or its derivative or salts, as well as mixtures thereof, may especially advantageously be used as hydrocolloids.

These hydrocolloids are capable of absorbing a wound healing substance, storing this substance as a repository and, if necessary, releasing it again in the presence of fluids. Surprisingly, it has been found that the fluid absorption and release of active substances also takes place in the presence of an aqueous phase or oil phase. In this connection, it has particularly been found that the release of wound healing substances occurs in a controlled manner and over a long period. It has further surprisingly been found that due to the presence of an aqueous phase and an oil phase, in the selection of active ingredients there are no particular limits with regard to their lipophilia or hydrophilia, i.e. as a result of the type of the emulsions that are formed, either a lypophilic active ingredient or a hydrophilic active ingredient may increasingly be released.

The hydrocolloid may be present in the form of fibers as well as in the form of particles and/or fibers that dispersed in the composition. In particular, the hydrocolloid may be present in the form of particles. Hydrocolloids that are present as particles and have an average particle diameter from 100 to 1000 um are preferred. The proportion of gel-forming particles in the composition is between 1 and 50 weight percent based on the total weight of the composition. The proportion of gel-forming particles may preferably be 1 to 40 weight percent, further preferably 1 to 30 weight percent and quite preferably 1 to 25 weight percent based on the total weight of the composition. The proportion of hydrocolloids in the composition is further preferably between 5 and 40 weight percent based on the total weight of the composition. The proportion of hydrocolloids may preferably be 5 to 30 weight percent, further preferably 10 to 25 weight percent, and quite preferably 15 to 25 weight percent based on the total weight of the composition.

Especially preferred are hydrocolloids that are present in particle form, whereby the particles have a water content of less than 10 weight percent, in particular less than 8 weight percent, in particular less than 5 weight percent based on the hydrocolloid particles. Quite especially preferred are particles that are water-free. In connection with the present invention, here and below this means that the gel-forming particles may contain traces of water, where the water content is 1 weight percent at the most based on the mass of the gel-forming particles.

Further, intermolecularly and/or intramolecularly linked or cross-linked hydrocolloids may preferably be used. These hydrocolloids are insoluble in water or saline solutions, for example, i.e. these hydrocolloids expand on addition of these fluids and demonstrate internal cohesion, so that the expanded particles are dispersed in the composition.

According to another form of the present disclosure, a composition comprises at least one hydrocolloid chosen from the group of cellulose derivatives or their salts, alginates or their derivatives, chitin or its derivative or its salts. In this connection, the origin of the hydrocolloid is immaterial, i.e. these hydrocolloids may be of plant or animal origin or be produced synthetically by means of microbiological methods, for example. It is also possible to use hydrocolloids of plant or animal origin that have been modified by means of chemical synthesis.

In connection with the present disclosure, the group of cellulose derivatives in particular includes cellulose ethers and cellulose esters as well as their salts. In this connection, hydroxyalkylcelluloses, in particular hydroxy-C1-6-alkylcellulose, like, for example, hydroxymethylcellulose, hydroxyethylcellulose, hydroxypropylcellulose, or hydroxybutylcellulose and quite particularly preferably hydroxymethylcellulose or hydroxyethylcellulose are used as cellulose ethers. Carboxyalkylcellulose, in particular carboxy-C1-6-alkylcellulose, like, for example, carboxymethylcellulose, carboxyethylcellulose, carboxypropylcellulose, or carboxybutylcellulose and quite particularly preferably carboxymethylcellulose or carboxyethylcellulose are used as cellulose esters.

According to another form, the composition comprises at least two different hydrocolloids. Here it has proven especially advantageous if the at least two hydrocolloids are chosen from the group of cellulose derivatives or its salts, in particular cellulose esters or their salts, alginates or their derivatives, chitin or its derivatives or its salts.

A synthetic polymer material chosen from the group of the polyacrylates or their derivatives or salts may further be used as a hydrocolloid. Here within the scope of the present invention, a polyacrylate is understood as a synthetic polymer comprising as monomer (M1) acrylic acid (2-propenic acid, $CH_2=CH-CO_2H$) and/or a salt thereof, having a monomer proportion of more than 60 weight percent of acrylic acid and/or a salt thereof (based on the total weight of the polyacrylate). In particular, according to the invention, polyacrylates comprise a monomer proportion of more than 80 weight percent of acrylic acid and/or a salt thereof and quite preferably more than 95 weight percent and/or a salt thereof based on the total weight of the polyacrylate. The polyacrylate may be present as a homopolymer, copolymer, or block polymer. If the polyacrylate is present as a copolymer or block polymer, the monomer proportion of the monomer M1 in the polymer in any case is more than 60%, in particular more than 80%, and quite preferably more than 95% based on the total weight of the polyacrylate. Apart from the monomer M1, these polyacrylate copolymers or polyacrylate block polymers may in particular include $\alpha,\beta$-unsaturated ethers (vinyl ethers), $\alpha,\beta$-unsaturated carbonic acids, or $\alpha,\beta$-unsaturated carbonic acid esters (vinyl esters). Of the comonomers M2 of the $\alpha,\beta$-unsaturated carbonic acids, methacrylic acid (2-methylpropenic acid), ethacrylic acid (2-ethylpropenic acid), crotonic acid (2-butenoic acid), sorbic acid (trans-trans-2,4-hexadienic acid), maleic acid (cis-2-butenedioic acid) or fumaric acid (trans-2-butenedioic acid) are particularly preferred. However, in a particularly preferred form of the invention it may also be provided that the polyacrylate consists of a) an acrylic acid homopolymer and/or b) a copolymer from i) acrylic acid and an acrylic acid salt, ii) from methacrylic acid and a methacrylic acid salt, or iii) from acrylic acid and methacrylic acid and their salts. However, it may further be provided that the polyacrylate is a mixture of different polyacrylates.

In this respect, the $\alpha,\beta$-unsaturated carbonic acid as well as the acrylic acid may be present in neutralized form as a salt, in non-neutralized form as a free acid or mixtures thereof. In particular, polyacrylates formed from acrylic acid and acrylic acid salts have proven especially effective. Alkaline metal or alkaline earth metal salts should particularly be highlighted in this case. In particular, polyacrylates consisting of homopolymers and/or copolymers, which comprise acrylic acid and/or sodium or potassium acrylate as monomers, have proven especially effective.

Furthermore, the teachings of the present disclosure provide hydrocolloids from the group of the linked and/or cross-linked polyacrylates. These polyacrylates preferentially comprise a) a homopolymer, which consists of the monomers M1 and is linked and/or cross-linked by means of a cross-linking agent, and/or b) a copolymer, which consists of the monomers M1 and M3, the monomer M1 being acrylic acid and/or a salt thereof, and the monomer M3 being chosen from the group of the cross-linking agents. This means that these polyacrylates comprise a polyacrylate subsequently linked by means of a cross-linking agent and/or a polyacrylate that has been copolymerized with acrylic acid and/or a salt thereof and a cross-linking agent.

It has particularly been shown that linked and/or cross-linked polyacrylates, which as cross-linking agents contain compounds V1 which have at least two ethylenically unsaturated groups in one molecule, or compounds V2, which have at least two functional groups, which can react with functional groups of the acrylic acid and/or a salt thereof in a condensation reaction, addition reaction, or ring-opening reaction, or compounds V3, which have at least one ethylenically unsaturated group and at least one functional group, which can react with functional groups of the acrylic acid and/or one of the salts thereof and/or the α,β-unsaturated comonomers in a condensation reaction, addition reaction, or ring-opening reaction are particularly effective. Here by means of the compounds V1, the polymers are cross-linked by radical polymerization of the ethylenically unsaturated groups of the cross-linking agent molecule with the monoethylenically unsaturated monomers of acrylic acid and/or one of its salts and/or one of the α,β-unsaturated comonomers, while with the compounds V2, cross-linking of the polymers via a condensation reaction of the functional groups with the functional groups of the acrylic acid and/or one of its salts or one of the α,β-unsaturated comonomers is accomplished Accordingly, with the compounds V3, cross-linking of the polymer via radical polymerization of the ethylenically unsaturated group as well as via a condensation reaction between the functional groups of the cross-linking agent and the functional monomer groups takes place.

Preferred compounds V1 are polyacrylic acid esters or polymethacrylic esters, which are obtained via reaction of a polyol, for example ethylene glycol(1,2-ethandiol), propylene glycol(1,2-propandiol), trimethylolpropane(2-ethyl-2-hydroxymethyl-1,3-propandiol), 1,6-hexanediol, glycerol(1,2,3-propantriol), pentaerythrite(2,2-bis(hydroxymethyl) propane-1,3-diol), polyethylene glycol (HO—(CH2-CH2-O)n-H with n=2 to 20), polypropylene glycol(HO—(CH(CH3)-CH2-O)n-H with n=2 to 20), of an aminoalcohol, a polyalkylene polyamine, like diethylene triamine or triethylene tetraamine for example, or of an alkoxylated polyol with acrylic acid or methacrylic acid. Especially preferred for the linked polyacrylates is a polyacrylate which is linked by means of a compound V1 which is a di-, tri- or tetraester of the polyacrylic acid or polymethacrylic acid, which is synthesized by reaction of an alkoxylated polyol, in particular an ethoxylated polyol, in particular ethoxylated ethylene glycol, ethoxylated propylene glycol, ethoxylated trimethylol propane, ethoxylated 1,6-hexanediol, or ethoxylated glycerol, with an average of n ethylene oxide units per hydroxy group of n=1 to 10, with acrylic acid or methacrylic acid. Further, polyvinyl compounds, polyallyl compounds, polymethylallyl compounds, acrylic acid esters or methacrylic acid esters of a monovinyl compound, acrylic acid esters or methacrylic acid esters of a monoallyl compound or monomethylallyl compound, preferably of the monoallyl compounds or monomethylallyl compounds of a polyol or an aminoalcohol. In this connection, reference is made to DE 195 43 366 and DE 195 43 368.

Additionally, hydrocolloids from the group of the polyacrylate superabsorbers are provided. Within the scope of the present disclosure, in this case, a polyacrylate superabsorber is understood as a polyacrylate with the above-mentioned features, which is capable of absorbing at least 15 times its own weight in physiological saline solution (0.9% NaCl solution, water).

Superabsorbers have been known in modern wound treatment for a long time. However, they are only used as a wound exudate absorbing medium. If these superabsorbers are used in this manner, solely the fluid balance of the wound or wound bed is regulated. Surprisingly, it has now also been found that polyacrylate superabsorbers are capable of absorbing fluid as well as releasing a wound healing substance in the presence of a water phase and an oil phase. This release also takes place in a controlled manner and over a long time.

In any case, the polyacrylate superabsorber may be present in the form of fibers or particles or gels. The polyacrylate superabsorber may be present in dry or already swollen form. In the swollen form, the polymer is present as gel-like discrete fibers or particles. According to the invention, in this case a hydrocolloid from the group of the polyacrylate superabsorbers may be present in the form of particles, which are mixed with water, physiological saline solution, or Ringer's solution, the particles being already present in swollen form.

Here especially preferred were polyacrylate superabsorbers, and in particular linked polyacrylate superabsorbers, which are present as particles, with the percentage of particles between 850 μm and 300 μm being at least 55%, in particular at least 65%, and most particularly 70% (measured according to EDANA 420.2.-02). In particular, superabsorbing polyacrylates are also preferred whose particle proportion smaller than 850 μm is at least 85%, in particular at least 90%, and quite particularly at least 95% based on all particles (measured according to EDANA 420.2-02).

As a wound healing substance releasable by a hydrocolloid according to the invention, a composition according to the invention or a wound contact layer according to the invention comprises in particular at least one substance chosen from the group of the vitamins or provitamins, carotenoids, analgesics, antiseptics, hemostyptics, antihistamines, antimicrobial metals or their salts, wound healing substances of plant origin or substance mixtures, plant extracts, enzymes, growth factors, and enzymatic inhibitors as well combinations thereof.

As analgesics according to the present disclosure, in particular nonsteroidal analgesics, in particular salicylic acid, acetylsalicylic acid and their derivatives, e.g. Aspirin®, aniline and their derivatives, acetaminophen, e.g. Paracetamol®, anthranilic acid and their derivatives, e.g. mefenamic acid, pyrazole or its derivatives, e.g. methamizole, Novalgin®, phenazone, Antipyrin®, isopropylphenazone, and quite particularly preferable are aryl acetic acids and their derivatives, heteroaryl acetic acids and their derivatives, aryl propionic acids and their derivatives and heteroaryl propionic acids and their derivatives, e.g. Indometacin®, Diclofenac®, Ibuprofen®, Naxoprofen®, Indomethacin®, Ketoprofen®, and Piroxicam® are suitable.

As growth factors according to the disclosure, the following should particularly be mentioned: aFGF (acidic fibroblast growth factor), EGF (epidermal growth factor), PDGF (platelet derived growth factor), rhPDGF-BB (Becaplermin), PDECGF (platelet derived endothelial cell growth factor), bFGF (basic fibroblast growth factor), TGF α (transforming growth factor alpha), TGF β (transforming growth factor beta), KGF (keratinocyte growth factor), IGF1/IGF2 (insulin-like growth factor) und TNF (tumor necrosis factor).

As vitamins or provitamins according to the disclosure, the fat-soluble or water-soluble vitamins vitamin A, group of retinoids, provitamin A, group of carotenoids, in particular β-carotene, vitamin E, group of tocopherols, in particular α-tocopherol, β-tocopherol, γ-tocopherol, δ-tocopherol, and α-tocotrienol, β-tocotrienol, γ-tocotrienol and δ-tocotrienol, vitamin K, phyllochinon, in particular phytomenadion or vitamin K of plant origin, vitamin C, L-ascorbic acid, vitamin B1, thiamine, vitamin B2, riboflavin, vitamin G, vitamin B3, niacin, nicotinic acid and nicotinic acid amide, vitamin B5, pantothenic acid, provitamin B5, panthenol or dexpanthenol, vitamin B6, vitamin B7, vitamin H, biotin, vitamin B9, folic acid as well as combinations thereof are suitable.

According to the disclosure, an agent that has germicidal, bactericidal, bacteriostatic, fungicidal, virucidal, virostatic and/or in general microbiocidal effect should be used as an antiseptic. According to the present disclosure, substances chosen from the group of resorcinol, iodine, iodine-povidon, chlorhexidine, benzalconium chloride, benzoic acid, benzoyl peroxide, or cetylpyridinium chloride are particularly suitable. Moreover, antimicrobial metals should also particularly be used as antiseptics. As antimicrobial metals, especially silver, copper or zinc as well as their salts, oxides or complexes in combinations thereof or alone may particularly be used.

In connection with the present disclosure, chamomile extracts, hamamelis extracts, e.g. *hamamelis virginia*, calendula extract, aloe extract, e.g. *aloe vera, aloe barbadensis, aloe ferox*, or *aloe vulgaris*, green tea extracts, seaweed extracts, seaweed extract, e.g. red seaweed or green seaweed extract, avocado extract, myrrh extract, e.g. *commophora molmol*, bamboo extracts as well as combinations thereof should in particular be used as wound healing substances or substance mixtures or plant extracts. According to the disclosure, extracts of leaves, blossoms, stalks or roots of plants or combinations thereof are in particular understood in this case.

Wound healing substances, which may be used individually or as a mixture of different wound healing substances, are particularly contained in the composition at a concentration of 0.01 to 30 weight percent, preferably at 0.01 to 15 weight percent, and quite particularly at 0.1 to 10 weight percent based on the weight of the hydrocolloids.

Hence, in another form a composition according to the invention comprises about 50 to about 99 weight percent of hydrophilic base, about 0.5 to about 40 weight percent of which comprises at least one O/W emulsifier, particularly an ionic O/W emulsifier or a W/O emulsifier, particularly a nonionic W/O emulsifier. The hydrophilic base contains about 1 to about 50 weight percent of dispersed hydrocolloids, which comprise at least one wound healing substance, the wound healing substance being chosen from the group of vitamins or provitamins, carotenoids, analgesics, antiseptics, hemostyptics, antihistamines, antimicrobial metals or their salts, wound healing substances of plant origin, or substance mixtures, plant extracts, enzymes, growth factors, and enzymatic inhibitors, as well as combinations thereof.

Further, an ointment comprising a medicinal composition of the above-described type is also the subject matter of the present disclosure. In particular, the subject matter of the present invention is an ointment comprising about 50 to about 99 weight percent of hydrophilic base, into which about 1 to about 50 weight percent of hydrocolloids are dispersed, which comprise at least one wound healing substance, whereby about 0.5 to about 40 weight percent of the hydrophilic base comprises at least one emulsifier. This ointment may be particularly applied to moderate to heavy exudating wounds, as, on the one hand, wound exudate can be absorbed in special quantities, and on the other hand, a moist environment is provided for the wound owing to the presence of hydrocolloids, which form a fluid reservoir. The hydrocolloids act as fluid dispensers and moisturizers at the same time, as well as an active ingredients repository for wound healing substances.

The subject matter of the present disclosure in particular is an ointment having less than about 10 weight percent of water comprising about 60 to 95% weight percent of a hydrophilic base, into which about 5 to about 40 weight percent of hydrocolloids are dispersed, about 0.5 to about 50 weight percent of the hydrophilic base comprising at least one emulsifier. This ointment may be particularly applied to moderate to heavy exudating wounds, as on the one hand wound exudate may be absorbed in special quantities with this ointment and, on the other hand, a moist environment is provided for the wound by the presence of hydrocolloids which form a fluid reservoir. In the ointment, the hydrocolloids act as fluid dispensers and moisturizers at the same time.

In one form, the ointment has less than 10 weight percent of water and further comprises 50 to 99% weight percent of hydrophilic base, into which 1 to 50 weight percent of hydrocolloids are dispersed, which comprise at least one releasable wound healing substance, the hydrophilic base comprising 10-40 weight percent of nonpolar fats and 0.5-40 weight percent of least one emulsifier. In a particularly preferred manner, the ointment according to the disclosure with less than 10 weight percent of water further comprises 50 to 99 weight percent of hydrophilic base, into which 1 to 50 weight percent of hydrocolloids are dispersed, which comprise one releasable wound healing substance, the hydrophilic base comprising 50-80 weight percent of monoglycerides, diglycerides, triglycerides and/or partial esters of glycerol oligomers, in particular of diglycerol or triglycerol, 20-35 weight percent of nonpolar fats, and 0.5-30 weight percent of at least one emulsifier. In particular, the antiseptic ointment is water-free.

The antiseptic ointment in one form has less than 10 weight percent of water and further comprises 60 to 95% weight percent of hydrophilic base, into which 5 to 40 weight percent of hydrocolloids are dispersed, the hydrophilic base comprising 20-35 weight percent of nonpolar fats and 0.5-30 weight percent of at least one emulsifier. In another form, the ointment according to the present disclosure with less than 10 weight percent of water further comprises 60 to 95 weight percent of hydrophilic base, into which 5 to 40 weight percent of hydrocolloids are dispersed, the hydrophilic base comprising 50-80 weight percent of monoglycerides, diglycerides, triglycerides and/or partial esters of glycerol oligomers, in particular of diglycerol or triglycerol, 20-35 weight percent of nonpolar fats, and 0.5-30 weight percent of at least one emulsifier. In particular, the ointment is water-free.

Hence the use of a composition having less than 10 weight percent of water, comprising 60 to 95 weight percent of a hydrophilic base, into which 5 to 40 weight percent of hydrocolloids are dispersed, 0.5 to 50 weight percent of the hydrophilic base comprising at least one emulsifier, for producing a wound treatment agent, is also the subject matter of the present disclosure. The agent may particularly be an ointment, which is further preferably used for the treatment of burn wounds or chronic wounds.

Moreover, the use of a composition having less than 10 weight percent of water, comprising 50 to 99 weight percent of hydrophilic base, into which 1 to 50 weight percent of hydrocolloids are dispersed, which comprise at least one releasable, wound healing substance, 0.6 to 40 weight percent of the hydrophilic base comprising at least one emulsifier for producing an antiseptic ointment for the treatment of burn wounds or chronic wounds, is also the subject matter of the present disclosure.

According to a further idea of the present disclosure, a wound contact layer comprising a carrier material and a medicinal composition is also the subject matter of the present invention. The subject matter of the present disclosure is a wound contact layer comprising a carrier material and a medicinal composition comprising 50 to 99 weight percent of hydrophilic base, into which 1 to 50 weight percent of hydrocolloids are dispersed, which comprise at least one wound healing substance, 0.5 to 50 weight percent of the hydrophilic base comprising at least one emulsifier.

In particular, the composition comprises less than 10 weight percent of water, in particular less than 5 weight percent of water, and quite particularly is water-free. The subject matter of the present invention in particular is a wound contact layer comprising a carrier material and a composition having less than 10 weight percent of water comprising 60 to 95% weight percent of hydrophilic base, into which 5 to 40 weight percent of hydrocolloids are dispersed, 0.5 to 50 weight percent of the hydrophilic base comprising at least one emulsifier. By means of the carrier material, the wound contact layer acquires an easily applicable form which may be applied evenly to a wound. Thus it may be provided that the composition is applied to at least one side of the carrier material or is applied in some other manner. It may also be provided that the composition is applied to both sides of the carrier material, or that the carrier material is completely impregnated with the composition. Here a wound contact layer according to the invention may further comprise all preferred properties or features of the above-described composition.

A further advantage compared with known wound contact layers is that on application to a wound, normally by trained staff by means of gloves, the wound contact layer according to the present invention does not adhere or stick to the gloves. Hence these wound contact layers are especially safe to handle.

Especially advantageous is the application of a composition, in particular an ointment, cream, or cream base to the carrier material in an amount of at least 50 g/m2, in particular of at least 100 g/m2, particularly preferably from 100 to 450 g/m2, and quite particularly preferably of 100 to 300 g/m2.

The wound contact layer especially preferably features a carrier material and a composition having less than 10 weight percent of water, the composition comprising 60 to 95% weight percent of hydrophilic base, into which 5 to 40 weight percent of hydrocolloids are dispersed, the hydrophilic base comprising 20-35 weight percent of nonpolar fats and 0.5-30 weight percent of at least one emulsifier. The wound contact layer according to the invention in particular comprises preferably a carrier material and a composition having less than 10 weight percent of water, the composition comprising 60 to 95% weight percent of hydrophilic base, into which 5 to 40 weight percent of hydrocolloids are dispersed, the hydrophilic base comprising 50-80 weight percent of monoglycerides, diglycerides, triglycerides, and/or partial esters of glycerol oligomers, in particular of diglycerol or triglycerol, 20-35 weight percent of nonpolar fats, and 0.5-30 weight percent of at least one emulsifier. In particular, the composition is water-free.

Owing to the presence of fatty acid glycerides in the composition, the skin surrounding a wound, the so called peripheral wound skin, is provided with therapeutic components that especially promote wound healing.

Various materials may be used as carrier material in this case. It has particularly been found that polymer films or foils, polymer foams, and nonwovens, as well as textile materials may be used. In a wound contact layer according to the invention, nonwovens as well as textile materials such as knitted, warp knitted, or woven fabrics may be used. Especially preferably, hydrophobic knitted, warp, knitted, or woven fabrics, which do not absorb fluids, may be used in this case. A wound contact layer according to the present invention comprises a polyamide warp knitted fabric as a carrier material.

If a textile carrier material is used, the material may in particular also be provided with openings, i.e. the carrier material is provided with holes or is available in the form of a mesh. It is particularly provided that the carrier material is a warp knitted or knitted, or woven fabric featuring holes whose maximum inside width is around 0.3 to 3.0 mm, preferably 0.5 to 2.5 mm, and especially preferably 0.5 to 2.0 mm in the unstretched state of the material. In this connection, the holes may have any shape, such circular, elliptical, square, hexagonal, or octagonal, for example. These warp knitted fabrics have a mass per unit area of at least 20 g/m2 up to a maximum of 120 g/m2.

It may further be provided that at least one wound healing substance is released by the wound contact layer. This particularly includes substances that have a fungicidal, bactericidal, or antimicrobial effect. In a particular embodiment, the wound contact layer comprises a hydrocolloid which for its part comprises at least one fungicidal, bactericidal, or antimicrobial substance. In this case, chitosan, silver, silver complexes, silver salts, zinc, zinc salts, or zinc complexes are particularly suitable.

The wound contact layer in one form features a carrier material and a medicinal composition having less than 10 weight percent of water, the composition comprising 60 to 95% weight percent of hydrophilic base, into which 5 to 40 weight percent of hydrocolloids comprising at least one releasable wound healing substance are dispersed, the hydrophilic base comprising 20-35 weight percent of nonpolar fats and 0.5-30 weight percent of at least one emulsifier. The wound contact layer according to the invention particularly preferably comprises a carrier material and a composition having less than 10 weight percent of water, the composition comprising 60 to 95% weight percent of hydrophilic base, into which 5 to 40 weight percent of hydrocolloids are dispersed, the hydrophilic base comprising 50-80 weight percent of monoglycerides, diglycerides, triglycerides, and/or partial esters of glycerol oligomers, in particular of diglycerol or triglycerol, 20-35 weight percent of nonpolar fats, and 0.5-30 weight percent of at least one emulsifier. In particular, the composition is water-free.

However, it may also be provided that a wound healing agent is applied directly to the carrier material. In a particularly advantageous manner, in a further embodiment of the wound contact layer, a nonwoven or textile material such as knitted, warp knitted, or woven fabric coated with an antimicrobial metal, preferably silver or silver salts, is used as a carrier material. When such a carrier material is used, the composition may be applied directly to a first side of the carrier material, to the metal or metal salt. Here it is especially advantageous if the composition if water-free.

That the carrier material comprises a composition at least on its first side is understood to mean that the composition is either disposed directly on the carrier with the metal, or that initially a continuous or discontinuous metal layer is applied to the first side, onto which in turn the composition is applied. It may also be desired that the composition be applied to both sides, in particular when the wound dressing is to be tamped into the wound. In this case it is advantageous if the metal application is applied to both sides or encloses the warp knitted fabric.

Here the composition, which in particular may be an ointment or cream, acts as a intermediary between the carrier material with the metal and the patient's wound. In this way, direct contact of the wound with the metal, and in particular adhesion thereon, may certainly be avoided. Furthermore, this ointment or cream may have a therapeutic effect on the peripheral wound skin. If the wound contact layer then comes in contact with the wound via the composition, the metal, e.g. silver, will be released from the wound dressing particularly via the wound exudate due to the mediation of the composition, reaching the wound via the composition. In this case, it may particularly be provided that elemental silver is used as the metal. The metal may be disposed as a coating on the carrier material or impregnated into the carrier.

The present disclosure further comprises a wound dressing, which comprises a cover layer and a wound contact layer. The wound contact layer here comprises a composition or an ointment comprising a hydrophilic base into which hydrocolloids are dispersed, the hydrophilic base comprising at least one emulsifier. The wound contact layer further comprises a composition or an ointment comprising a hydrophilic base into which hydrocolloids are dispersed, which comprise at least one releasable, wound healing substance, the hydrophilic base comprising at least one emulsifier. In particular, the present invention comprises a wound dressing which comprises a cover layer and a wound contact layer, the wound contact layer having a medicinal composition which comprises 50 to 99 weight percent of hydrophilic base, into which 1 to 50 weight percent of hydrocolloids are dispersed, which comprise at least one releasable, wound healing substance, 0.5 to 50 weight percent of the hydrophilic base comprising at least one emulsifier. In particular, the present invention comprises a wound dressing that comprises a cover layer and a wound contact layer, the wound contact layer comprising a composition having less than 10 weight percent of water, which comprises 60 to 95 weight percent of hydrophilic base, into which 5 to 40 weight percent of hydrocolloids are dispersed, 0.5 to 50 weight percent of the hydrophilic base comprising at least one emulsifier. In this connection, a wound dressing according to the invention may further feature all the preferred properties or features, in particular of the above-described wound contact layer as well as of the above-described composition.

In particular, the present disclosure comprises a wound dressing, comprising a cover layer and a wound contact layer, the wound contact layer comprising a carrier material and a composition having less than 10 weight percent of water, which further comprises 60 to 95 weight percent of hydrophilic base, into which 5 to 40 weight percent of hydrocolloids are dispersed, 0.5 to 50 weight percent of the hydrophilic base comprising at least one emulsifier.

According to a further development of the present disclosure, the present invention also comprises a wound dressing which comprises a cover layer, an absorbent layer, and a wound contact layer, the wound contact layer comprising a composition having less than 10 weight percent of water, which comprises 60 to 95 weight percent of hydrophilic base, with 0.5 to 50 weight percent comprising at least one emulsifier, into which 5 to 40 weight percent of hydrocolloids are dispersed.

According to a further development of the disclosure, the present invention also comprises a wound dressing which comprises a cover layer, an absorbent layer, and a wound contact layer, the wound contact layer comprising a composition having less than 10 weight percent of water, which comprises 50 to 99 weight percent of hydrophilic base with 0.5 to 50 weight percent comprising at least one emulsifier, into which 1 to 50 weight percent of hydrocolloids are dispersed, which comprise at least one releasable wound healing substance.

The wound dressing may particularly comprise a polymer foil or a polymer film as a cover layer. In one form, the wound dressings are polymer films which have high water vapor permeability. For this purpose, polyurethane, polyether urethane, polyester urethane, polyether polyamide copolymer, polyacrylate or polymethacrylate films are particularly suitable. Polyurethane film, polyester urethane film, or polyether urethane films are particularly preferred as polymer films. However, polymer films are quite especially preferred which feature a thickness of 15 to 50 um, in particular 20 to 40 um, and quite particularly between 25 and 30 um. The water vapor permeability of the polymer film of the wound dressing is preferably at least 750 g/m2/24 h, in particular at least 1000 g/m2/24 h, and quite particularly at least 2000 g/m2/24 h (measured according to DIN 13726).

Furthermore, it may be provided that the wound dressing according to the disclosure is available as a so called island dressing. In this case, the wound contact layer has a smaller contact area than the cover layer, i.e. the wound contact layer is enclosed by the cover layer along its circumference. The cover layer may have a pressure sensitive adhesive or be provided with an adhesive so that the entire wound dressing may adhere or stick to the patient's skin. This adhesive may be applied to the entire surface or discontinuously in certain areas. The adhesive to be used may be a conventional adhesive, in particular an acrylate adhesive or a pressure-sensitive adhesive based on polyurethanes. It is preferably a gel-based adhesive, in particular based on polyurethanes, in particular aqueous polyurethanes. Especially preferably it is a hydrogel-based adhesive, in particular based on aqueous acrylates.

According to a refinement of the present disclosure, the wound dressing may have a cover layer which is entirely coated with an adhesive. The water vapor permeability of this carrier material with the adhesive is preferably at least 1000 g/m2/24 h, especially preferably at least 1200 g/m2/24 h, and quite preferably 2000 g/m2/24 h (measured according to DIN EN 13726).

A wound dressing according to the present invention may be available in any geometrical shape, for example triangular, round, oval or quadratic, rectangular, or any symmetrical or asymmetrical shape.

It may further be provided that the wound dressing according to the invention has other layers, which may have different functions. According to a further development of the present invention, the wound dressing has at least one more layer. This layer may preferably be a release layer to protect against contamination, which, with the wound dressing being in a suitable state for use, is applied to the side of the wound contact layer that will be in contact with the wound. It may also be provided that the wound dressing has at least another layer between the wound contact layer and the cover layer. This other layer may be an absorbent layer, such as an absorbent hydrophilic foam layer made of polyurethane, for example.

Hence the use of a medicinal composition having less than 10 weight percent of water, comprising 60 to 95 weight percent of hydrophilic base, into which 5 to 40 weight percent of hydrocolloids are dispersed, 0.5 to 50 weight percent of the hydrophilic base comprising at least one emulsifier for producing a wound contact layer or a wound dressing, in particular for the treatment of burn wounds or chronic wounds, is also the subject matter of the present invention.

In a particular embodiment of the invention, a wound dressing according to the invention is disposed in a package. In this connection, it is particularly provided that the package is a sterile package. In a further particular embodiment of the present invention it is provided, that the system comprising a wound contact layer of the described type and a separate wound dressing is disposed in one package. Hereby it is particularly provided that the package is a sterile package. In an especially preferred embodiment of this system, each individual component or each group of components is in separate inner packages in the package or sterile package. It may also be provided that each inner package is a sterile inner package.

It should be emphasized at this point that the here described features of the alternative or preferred embodiments of the present inventions are not to be restricted to the individual alternatives or preferred embodiments. Rather, the combination of embodiments and/or combination of the individual features of the alternative and preferred types are likewise to be included in the embodiment according to the invention. Nor should the invention be understood as constrained by the following description of the drawings.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 2:
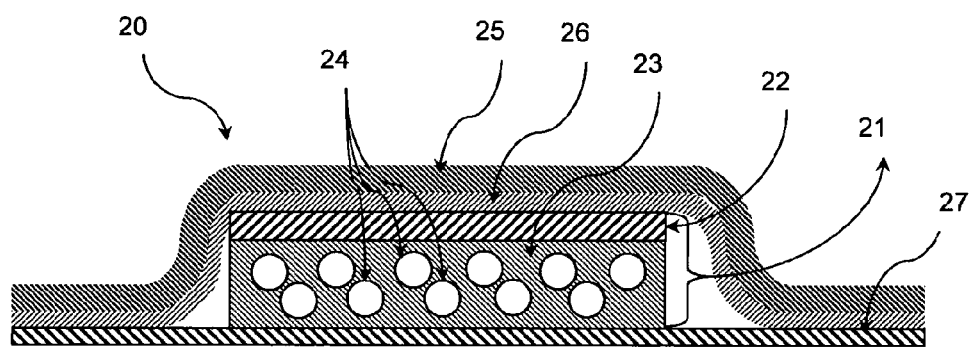

The present invention is exemplified hereinafter by reference to the drawings and examples. The drawings show:

FIG. 1: Cross-section of the wound contact layer;

FIG. 2: Cross-section of the wound dressing; and

Figure 3:
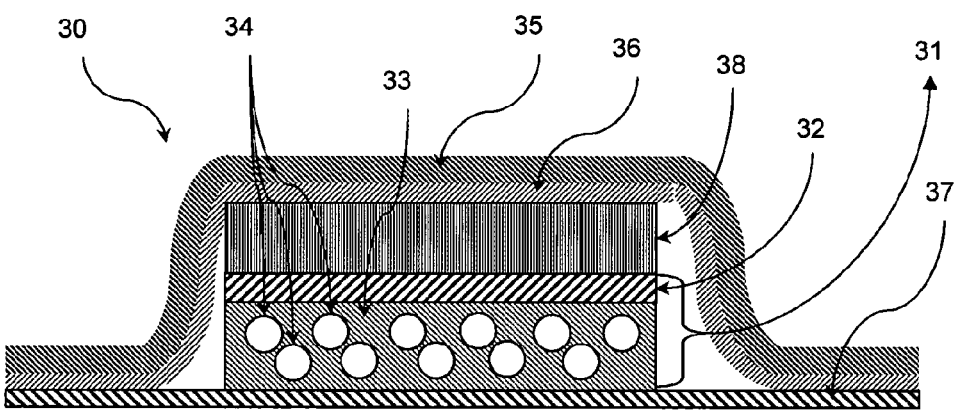

FIG. 3: Cross-section of the alternative wound dressing.

DETAILED DESCRIPTION

Examples

1) Composition # 1

| Commercial name No. (Manufacturer) | Description - INCI, function | Content, weight |
|---|---|---|
| 1 IMWITOR 780 K (Sasol, Witten - Germany) | Isostearyl diglyceryl succinate, nonionic W/O emulsifier HLB 3.7 | 5.0 |
| 2 IMWITOR 900 K (Sasol, Witten - Germany) | Glyceryl stearate Co-emulsifier | 4.0 |
| 3 SOFTISAN 100 (Sasol, Witten - Germany) | Hydrogenated cocoglycerides, polar fat | 4.0 |
| 4 SOFTISAN 378 (Sasol, Witten - Germany) | Caprylic/capric/myristic/ stearic triglycerides, polar fat | 23.0 |
| 5 SOFTISAN 649 (Sasol, Witten - Germany) | Bis-diglyceryl polyacyladipate-2, polar fat | 19.0 |
| 6 MERKUR Vaseline 115 (Merkur Vaseline GmbH & Co. KG, Hamburg - Germany) | Petrolatum, nonpolar lipid | 25.0 |
| 7 Aquacel ® Ag (Convatec Vertriebs-GmbH, Munich - Germany) | Sodium carboxymethylcellulose fibers with silver ions | 20.0 |

Production of Composition #1:

Phase A (components 1 to 6) is melted at around 75-80° C. and stirred. Phase B (component 7, fibers present as individual fibers having a length of 2-10 mm) is subsequently dispersed into phase A with intense stirring. The ointment mass is cooled with intense stirring so that a fine crystal structure is created. The drop point of the composition is 46° C. (determined according to Ph. Eur. 2002, method 2.2.17).

Composition # 2

| Commercial name No. (Manufacturer) | Description - INCI, function | Content weight percent |
|---|---|---|
| 1 IMWITOR 377 (Sasol, Witten - Germany) | Glyceryl laurate citrate, ionic W/O emulsifier | 5.0 |
| 2 IMWITOR 900 K (Sasol, Witten - Germany) | Glyceryl stearate Co-emulsifier | 4.0 |
| 3 SOFTISAN 100 (Sasol, Witten - Germany) | Hydrogenated cocoglycerides, polar fat | 4.0 |
| 4 SOFTISAN 378 (Sasol, Witten - Germany) | Caprylic/capric/myristic/ stearic triglyceride, polar fat | 23.0 |
| 5 SOFTISAN 649 (Sasol, Witten - Germany) | Bis-diglyceryl polyacyladipate-2, polar fat | 19.0 |
| 6 MERKUR Vaseline 115 (Merkur Vaseline GmbH & Co. KG, Hamburg - Germany) | Petrolatum, nonpolar lipid | 25.0 |
| 7 AquaceI ® Ag (Convatec Vertriebs-GmbH, Munich - Germany) | Sodium carboxymethylcellulose fibers with silver ions | 20.0 |

Production of Composition #2:

Phase A (components 1 to 6) is melted at around 75-80° C. and stirred. Phase B (component 7, fibers present as individual fibers having a length of 2-10 mm) is subsequently dispersed into phase A with intense stirring. The ointment mass is cooled with intense stirring so that a fine crystal structure is created. The drop point of the composition is 48° C. (determined according to Ph. Eur. 2002, method 2.2.17).

3) Wound Contact Layer #1

The present wound contact layer has the configuration shown in FIG. 1. Thus the wound contact layer (10) features a carrier material (1) made of a hydrophobic 100% polyester warp knitted fabric (Theodor Preuss GmbH & Co. KG, Ubstadt-Weiher-Germany), which is coated on both sides and/or surfaces with the composition 2a and 2b according to the invention analogously to example #1. The difference is that instead of silver-doped CMC fibers, silver-doped CMC particles having an average particle size of 300 μm were used. Accordingly, the composition consists of a hydrophilic base (13) analogous to example #1 and CMC particles (14), which are charged with releasable silver ions at a volume of 10 weight percent based on the particle quantity. The composition completely wets the carrier material, the applied quantity being 200 g/m2 on each side. The warp knitted carrier fabric has a mass per unit area of 63 g/m2 (unstretched) and features around 40 hexagonal holes per 100 cm (not illustrated in FIG. 1). The maximum inside width of the openings is 2 mm. The wound contact layer features good cohesion and may be applied especially well to a wound to be treated.

4) Wound Contact Layer #2

This wound contact layer also features a configuration similar to FIG. 1. In this wound contact layer (10) the composition features the components indicated in example No. 1 The carrier material (1) consists of a hydrophobic 100% polyamide warp knitted fabric (Theodor Preuss GmbH & Co. KG, Ubstadt-Weiher-Germany), having a mass per unit area of approximately 90 g/m2 (unstretched) and featuring approximately 46 hexagonal holes per 100 cm (not illustrated in FIG. 1). The maximum inside width of the openings is 0.8-1.0 mm. The coating weight of the composition is 240 g/m2.

The textile carrier material is coated with the hydrophilic composition by running the carrier material through a warm bath (40° C.) of the hydrophilic composition 1, 2 or an analogous composition with silver-doped CMC particles by means of a guide roller. After passing through the bath, the excess volume of the transferred composition is stripped off by means of a squeegee. The coated material is brought to room temperature, assembled, packaged, and sterilized.

5) Wound Contact Layer #3

This wound contact layer also features a configuration similar to FIG. 1. In this wound contact layer (10) the composition features the components indicated in example No. 2

The carrier material (1) consists of a hydrophobic 100% polyamide warp knitted fabric (Theodor Preuss GmbH & Co. KG, Ubstadt-Weiher-Germany), having a mass per unit area of approximately 80 g/m2 (unstretched) and comprising approximately 40 hexagonal holes per 100 cm (not illustrated in FIG. 1). The maximum inside width of the holes is 1.2-1.5 mm. The coating weight of the composition is 330 g/m2.

The textile material is coated with the hydrophilic composition by running the carrier material through a warm bath (60° C.) of the hydrophilic composition #2 by means of a guide roller. After passing through the bath, the excess volume of the transferred composition is stripped off by means of a squeegee. The coated material is brought to room temperature, assembled, packaged, and sterilized.

6) Wound Dressing #1

FIG. 2 shows the wound dressing (20) according to the present invention as a so-called island dressing. The wound dressing consists of a cover layer (24) and a wound contact layer (21). For its part, the wound contact layer consists of a carrier material (22), which is a hydrophobic polyester fiber nonwoven fabric, which is coated with a composition that is analogous to the composition (23) according to example No. 2. The difference is that silver-doped alginate particles are used in this case. Thus the composition consists of a hydrophilic base (23), into which alginate particles charged with releasable ionic silver are dispersed. The composition completely coats the polyester nonwoven fabric (water-jet reinforced, mass per unit area 50 g/m2) with a coating quantity of 180 g/m2. The wound contact layer is covered with a cover layer (24), whose surface is fully coated with a polyacrylate adhesive (25). The cover layer is a 30-μm thick polyurethane film having a water vapor permeability of 1100 g/m2/24 h, which reaches the wound contact layer beyond its circumferential border on all sides so that the wound contact layer may be adhered to a patient's skin by means of the adhesive borders of the cover layer (26a, 26b). The wound contact layer (22) is at the same time fixed to the cover layer by means of the adhesive (25).

7) Wound Dressing #2

FIG. 3 shows a further wound dressing (30) according to the invention, which compared with the wound dressing (20) shown in FIG. 2 has an additional absorbent layer (37). This additional absorbent layer (37) consists of hydrophilic, open-cell polyurethane foam with a mass per unit area of 500 g/m2 and a 5-mm thickness. The absorbent layer is fixed to the cover layer by means of an acrylate dispersion adhesive. The cover layer consists of a polyurethane film having a 25 μm thickness and a water vapor permeability of 1200 g/m2/24 h. The wound contact layer (31) consists of a warp knitted polyamide fabric (32), which is coated with a composition (33) according to the example No 1 (150 g/m2). The warp knitted polyamide fabric (Theodor Preuss GmbH & Co, KG, Ubstadt-Weiher-Germany) features 45 hexagonal holes per 100 cm (not shown in FIG. 3). The maximum inside width is 0.8 to 1.0 mm. The mass per unit area is 86 g/m2. The wound dressing should especially be used with heavy exudating wounds. Owing to the presence of triglycerides in the composition, the wound dressing treats the peripheral wound skin without adhering to the wound, even when used for a longer period.

What is claimed is:

1. A medicinal composition for wound treatment comprising about 50 to about 99 weight percent of hydrophilic base, into which about 1 to about 50 weight percent of hydrocolloids are dispersed, about 0.5 to about 50 weight percent of the hydrophilic base comprising at least one emulsifier and the hydrophilic base further comprising about 20-80 weight percent of the group consisting of monoglycerides, diglycerides, and/or triglycerides, and/or full or partial esters of glycerol oligomers, characterized in that the hydrocolloids comprise at least one releasable wound healing substance and the hydrophilic base contains up to 1 weight percent of water.

2. The composition according to claim 1, characterized in that the hydrophilic base is selected from the group consisting of a cream, a cream base, or an ointment.

3. The composition according to claim 1, characterized in that the hydrocolloids are present in the form of particles.

4. The composition according to claim 1, characterized in that the hydrocolloids are chosen from the group consisting of celluloses or derivatives or their salts, as well as alginic acids or their derivatives or salts, as well as polyacrylates or their derivatives or salts.

5. The composition according to claim 1, characterized in that the wound healing substance is chosen from the group consisting of vitamins or provitamins, carotenoids, analgesics, antiseptics, hemostyptics, antihistamines, antimicrobial metals or their salts, wound healing substances of plant origin or substance mixtures, plant extracts, enzymes, growth factors, and enzymatic inhibitors, as well combinations thereof.

6. The composition according to claim 1, characterized in that the hydrophilic base further comprises about 10 to 30 weight percent of nonpolar lipids selected from the group consisting of Vaselines, petrolatums, paraffin oils, or waxes.

7. The composition according to claim 1, characterized in that the emulsifier is one of an ionic oil in water emulsifier and a nonionic water in oil emulsifier.

8. The composition according to claim 1 provided in the form of an ointment.

9. A wound contact layer having the medicinal composition according to claim 1 and comprising a carrier material for the composition.

10. The wound contact layer according to claim 9, characterized in that the carrier material is selected from the group consisting of a nonwoven, knitted, warp knitted, woven, hydrophobic knitted, hydrophobic warp knitted, and a hydrophobic woven fabric.

11. The wound contact layer according to claim 9, characterized in that the carrier material is a warp knitted polyamide fabric.

12. The wound contact layer according to claim 9, wherein the composition is provided in the form of an ointment.

13. A wound dressing having the medicinal composition according to claim 1 and comprising a carrier material for the composition and a cover layer.

14. The wound dressing according to claim 13, characterized in that the wound dressing further comprises an absorbent layer, in particular a hydrophilic polyurethane foam, which is adjacent to the wound contact layer.

15. The wound dressing according to claim 13, wherein the composition is provided in the form of an ointment.

* * * * *